United States Patent [19]
DeCoster et al.

[11] Patent Number: 6,159,914
[45] Date of Patent: Dec. 12, 2000

[54] DETERGENT COSMETIC COMPOSITIONS AND USE THEREOF COMPRISING AN AMINOSILICONE AND A CATIONIC POLYMER

[75] Inventors: Sandrine DeCoster, Epinay sur Seine; Bernard Beauquey, Clichy, both of France

[73] Assignee: L'Oreal, Paris, France

[21] Appl. No.: 09/055,666

[22] Filed: Apr. 7, 1998

[30] Foreign Application Priority Data

Apr. 7, 1997 [FR] France ................................. 97 04219

[51] Int. Cl.$^7$ ............................... C11D 1/29; C11D 1/90; C11D 3/37; C11D 9/36

[52] U.S. Cl. .................... 510/119; 510/121; 510/122; 510/123; 510/125; 510/242; 510/466; 510/490; 510/504; 510/426

[58] Field of Search ...................... 510/119, 121, 510/122, 123, 125, 242, 466, 490, 504, 426

[56] References Cited

U.S. PATENT DOCUMENTS

| | | |
|---|---|---|
| 2,258,378 | 10/1941 | Collman . |
| 2,781,354 | 2/1957 | Mannheimer . |
| 4,693,935 | 9/1987 | Mazurek ................................. 428/352 |
| 4,728,571 | 3/1988 | Clemens et al. ........................ 428/352 |
| 4,972,037 | 11/1990 | Garbe et al. ............................. 526/245 |
| 5,089,252 | 2/1992 | Grollier et al. ............................ 424/47 |
| 5,152,914 | 10/1992 | Forster et al. ............................ 252/174 |
| 5,650,383 | 7/1997 | Dubief et al. ............................. 510/122 |

FOREIGN PATENT DOCUMENTS

| | | |
|---|---|---|
| 0 059 428 | 9/1982 | European Pat. Off. . |
| 0 089 749 | 9/1983 | European Pat. Off. . |
| 0 115 252 | 8/1984 | European Pat. Off. . |
| 0 342 834 | 11/1989 | European Pat. Off. . |
| 0 392 320 | 10/1990 | European Pat. Off. . |
| 0 412 704 | 2/1991 | European Pat. Off. . |
| 0 412 707 | 2/1991 | European Pat. Off. . |
| 0 521 748 | 1/1993 | European Pat. Off. . |
| 0 582 152 | 2/1994 | European Pat. Off. . |
| 2 589 476 | 5/1987 | France . |
| 2 641 185 | 7/1990 | France . |
| 4139115 | 5/1992 | Japan . |
| 5043427 | 2/1993 | Japan . |
| 5221830 | 8/1993 | Japan . |
| 6234618 | 8/1994 | Japan . |
| 8217643 | 8/1996 | Japan . |
| WO 93/08787 | 5/1993 | WIPO . |
| WO 93/23009 | 11/1993 | WIPO . |
| WO 93/23446 | 11/1993 | WIPO . |
| WO 94/06403 | 3/1994 | WIPO . |
| WO 95/00578 | 1/1995 | WIPO . |
| WO 95/01152 | 1/1995 | WIPO . |
| WO 95/03776 | 2/1995 | WIPO . |
| WO 96/32919 | 10/1996 | WIPO . |

OTHER PUBLICATIONS

English Language Derwent Abstract of FR 2 589 476.
English Language Derwent Abstract of FR 2 641 185.
English Language Derwent Abstract of EP 0 115 252.
Derwent Abstract of JP 8217643.
Derwent Abstract of JP 6234618.
Derwent Abstract of JP 5221830.
Derwent Abstract of JP5043427.
Derwent Abstract of JP 4139115.

*Primary Examiner*—Necholus Ogden
*Assistant Examiner*—Charles Boyer
*Attorney, Agent, or Firm*—Finnegan, Henderson, Farabow, Garrett & Dunner, L.L.P.

[57] ABSTRACT

Novel detergent compositions comprising, in a cosmetically acceptable medium, (A) a washing base comprising at least one ether sulphate anionic surfactant and at least one surfactant of alkylbetaine type, and (B) a conditioning system comprising at least one cationic polymer, preferably dimethyldiallylammonium, and at least one aminosilicone, and uses thereof.

39 Claims, No Drawings

DETERGENT COSMETIC COMPOSITIONS AND USE THEREOF COMPRISING AN AMINOSILICONE AND A CATIONIC POLYMER

Applicants reference herein the patent applications of SANDRINE DECOSTER and BERNARD BEAUQUEY for COSMETIC COMPOSITIONS CONTAINING A CATIONIC POLYMER OF LOW MOLECULAR MASS AND A SILICONE, AND USES THEREOF and for DETERGENT COSMETIC COMPOSITIONS AND USE THEREOF, filed on even date herewith and incorporate the disclosure thereof specifically by reference herein.

The present invention relates to novel cosmetic compositions with improved properties, intended both for cleaning and conditioning keratin substances, and comprising, in a cosmetically acceptable vehicle, a washing base comprising surfactants with detergent power, in which cationic polymers in combination with aminosilicones are also present as conditioners. The invention also relates to the use of the compositions in the above-mentioned cosmetic application.

It is common to use detergent compositions based essentially on standard surfactants of anionic, nonionic and/or amphoteric type in particular, but more particularly of anionic type, to clean and/or wash the skin or the hair. These compositions are applied to wet hair or skin and the lather generated by massaging or rubbing with the hands removes, after rinsing with water, the various types of soiling which are initially present on the skin or hair.

Admittedly these base compositions are of good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fiber, this damage being associated in particular with the gradual removal of the lipids or proteins contained in or on the surface of this fiber.

Thus, in order to improve the cosmetic properties of the above detergent compositions, and more particularly those which are to be applied to sensitized hair (i.e. hair which has been damaged or made brittle, in particular under the chemical action of atmospheric agents and/or hair treatments such as permanent-waving, dyeing or bleaching), it is now common to introduce additional cosmetic agents known as conditioners into these compositions, these conditioners being intended mainly to repair or limit the harmful or undesirable effects induced by the various treatments or aggressions to which the hair fibers are subjected more or less repeatedly. These conditioners may, of course, also improve the cosmetic behaviour of natural hair.

The conditioners most commonly used to date in shampoos are cationic polymers, silicones and/or silicone derivatives, which give washed, dry or wet hair an ease of disentangling, softness and smoothness which are markedly better than that which can be obtained with corresponding cleaning compositions from which they are absent.

On sensitized hair, in order to obtain the cosmetic effects of silicones over the entire length of the hair fiber, combinations of silicones and cationic polymers are preferably used.

However, despite the progress made recently in the field of shampoos based on silicones and cationic polymers, these shampoos are not really completely satisfactory, and as such a strong need still exists currently as regards being able to provide novel products which give better performance with respect to one or more of the cosmetic properties mentioned above.

The present invention is directed towards satisfying such a need.

Thus, after considerable research conducted in this matter, the inventors have now found, entirely surprisingly and unexpectedly, that by using (A) a specific washing base and (B) a conditioning system comprising at least one specific cationic polymer and at least one aminosilicone, as defined below, it is possible to obtain detergent compositions which have excellent cosmetic properties, in particular with respect to the disentangling, the softness, the suppleness and the volume of treated hair, while at the same time retaining their good intrinsic washing power.

Thus, according to the present invention, novel detergent compositions are now proposed, comprising, in a cosmetically acceptable medium, (A) a washing base comprising at least one anionic surfactant of alkyl ether sulphate type and at least one amphoteric surfactant of $C_8$–$C_{20}$ alkylbetaine type and (B) a conditioning system comprising at least one aminosilicone and at least one cationic polymer selected from homopolymers containing, as main constituents of the chain, units corresponding to formulae (I) and/or (I'):

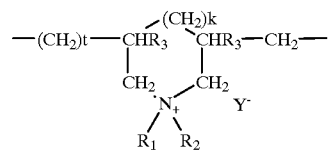

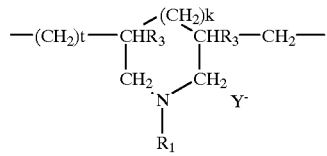

in which k and t are equal to 0 or 1, the sum k + t being equal to 1;

$R_3$ independently denotes a hydrogen atom or a methyl radical;

$R_1$ and $R_2$ independently denote an alkyl group having from 1 to 22 carbon atoms, a hydroxyalkyl group in which the alkyl group preferably has 1 to 5 carbon atoms, a lower (1 to 5 carbon atoms) amido alkyl group, or $R_1$ and $R_2$ can denote, together with the nitrogen atom to which they are attached, heterocyclic groups such as piperidyl or morpholinyl; and $Y^-$ is an anion such as bromide, chloride, acetate, borate, citrate, tartrate, bisulphate, bisulphite, sulphate or phosphate.

The subject of the invention is also the cosmetic use of the above compositions for cleaning and conditioning keratin substances such as the hair and the skin.

The compositions can be used, for example, for removing make-up from keratin substances such as the skin (for example the face, the neck or the lips), the eyelashes or the eyebrows.

However, other characteristics, aspects and advantages of the invention will emerge even more clearly on reading the description which follows, as well as the concrete, but in no way limiting, examples intended to illustrate it.

As indicated above, the essential constituents forming part of the composition of the hair products of the invention are (A) a washing base, (B) a conditioning system comprising (i) at least one aminosilicone and (ii) at least one specific cationic polymer.

A-Washing Base:

The compositions in accordance with the invention necessarily comprise a washing base, which is generally aqueous, comprising one or more anionic surfactants of alkyl ether sulphate type and one or more $C_8$–$C_{20}$ alkylbetaine amphoteric surfactants.

The minimum amount of washing base is that which is just sufficient to give the final composition a satisfactory foaming power and/or detergent power, and excessive amounts of washing base do not really afford additional advantages.

Thus, according to the invention, the washing base can preferably represent from 2% to 50% by weight, more preferably from 10% to 35% by weight and even more preferably from 12% to 25% by weight, of the total weight of the final composition.

(i) Anionic surfactant(s) of alkyl ether sulphate type:

The anionic surfactants of alkyl ether sulphate type which can preferably be used, alone or as mixtures, in the context of the present invention are salts (in particular alkaline salts, especially sodium salts, ammonium salts, amine salts, amino alcohol salts or magnesium salts) of alkyl ether sulphates, alkylamido ether sulphates, alkylaryl ether sulphates; alkyl ether sulphosuccinates, the alkyl radical of all these various compounds preferably containing from 8 to 24 carbon atoms, and the aryl radical preferably denoting a phenyl or benzyl group.

The average number of ethylene oxide or propylene oxide groups can range in particular from 2 to 50 and more particularly from 2 to 10.

Among these anionic surfactants, $C_8$–$C_{14}$ and more particularly $C_{12}$–$C_{14}$ alkyl ether sulphate salts are preferably used. These salts comprise in particular from 2 to 5 ethylene oxide groups.

The anionic surfactants are preferably present in a proportion of from 1 to 50% by weight, more preferably from 5 to 20% by weight, relative to the total weight of the composition.

(ii) Amphoteric surfactant(s):

According to the invention, the amphoteric surfactants must be selected from ($C_8$–$C_{20}$)alkylbetaines of formula:

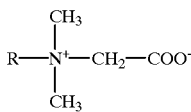

in which

R denotes a linear or branched $C_8$–$C_{20}$, more preferably $C_{10}$–$C_{14}$ and even more particularly $C_{12}$–$C_{14}$, alkyl radical.

In particular, the cocobetaine sold by the company Henkel under the name DEHYTON AB 30 is preferably used.

The amphoteric surfactants are preferably present in a proportion of from 1 to 50% by weight, more preferably from 1 to 20% by weight, relative to the total weight of the composition.

B-Conditioning System (i)—Aminosilicones

According to an essential characteristic of the detergent compositions in accordance with the invention, these compositions also contain at least one aminosilicone.

Hereinabove and hereinbelow, in accordance with the definition generally accepted, the term silicone or polysiloxane is understood to denote any organosilicon polymer or oligomer with a linear or cyclic, branched or crosslinked structure, of variable molecular weight, obtained by polymerization and/or polycondensation of suitably functionalized silanes, and including a repetition of main units in which the silicon atoms are connected together by oxygen atoms (siloxane bond ≡Si—O—S≡), optionally substituted hydrocarbon radicals being linked directly via a carbon atom to the said silicon atoms. The most common hydrocarbon radicals are alkyl radicals, especially $C_1$–$C_{10}$ alkyl radicals and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, in particular, hydrogen, halogen and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, amide groups, acyloxy or acyloxyalkyl radicals, amphoteric or betaine groups, anionic groups such as carboxylates, thioglycolates, sulphosuccinates, thiosulphates, phosphates and sulphates, this list obviously being in no way limiting (so-called "organomodified" silicones).

According to the invention, the term aminosilicone denotes any silicone containing at least one primary, secondary or tertiary amine or a quaternary ammonium group. Mention may thus be made of:

(a) the polysiloxanes referred to in the CTFA dictionary as "amodimethicone" and corresponding to the formula:

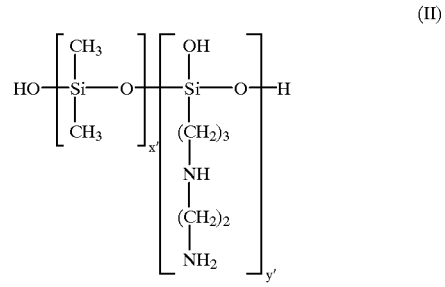

(II)

in which x' and y' are integers selected to determine the molecular weight, and generally such that the weight-average molecular weight ranges from 5000 to 500,000 approximately;

(b) aminosilicones corresponding to the formula:

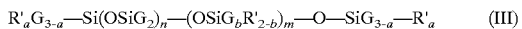

(III)

in which:

G independently is a hydrogen atom or a phenyl, OH or $C_1$–$C_8$alkyl group, for example methyl, a independently denotes the number 0 or an integer from 1 to 3, in particular 0, b independently denotes 0 or 1, and in particular 1, m and n are numbers such that the sum (n +m) can range especially from 1 to 2000 and in particular from 50 to 150, it being possible for n to denote a number from 0 to 1999 and especially from 49 to 149 and it being possible for m to denote a number from 1 to 2000 and especially from 1 to 10;

R' independently is a monovalent radical of formula —$C_qH_{2q}$L in which q is a number from 2 to 8 and L is an optionally quaternized amine group selected from the groups:

—NR"—$CH_2$—$CH_2$—N'(R")$_2$

—N(R")$_2$

—N⊕(R")$_3$A⁻

—NH⊕(R")$_2$A$^-$
—NH$_2$⊕(R")A$^-$
—N(R")—CH$_2$—CH$_2$—N⊕R"H$_2$A$^-$,
in which R" independently can denote hydrogen, phenyl, benzyl, or a saturated monovalent hydrocarbon radical, for example an alkyl radical having from 1 to 20 carbon atoms, and A$^-$ represents a halide ion such as, for example, fluoride, chloride, bromide or iodide.

A product corresponding to this definition is the silicone known as "trimethylsilylamodimethicone", corresponding to the formula:

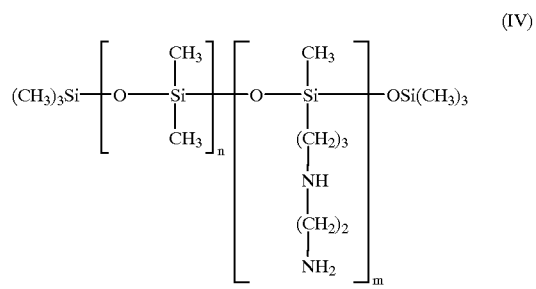

(IV)

in which n and m have the meanings given above (cf. Formula III).

Such polymers are described, for example in patent application EP-A-95238, the disclosure of which is specifically incorporated by reference herein.

(c) aminosilicones corresponding to the formula:

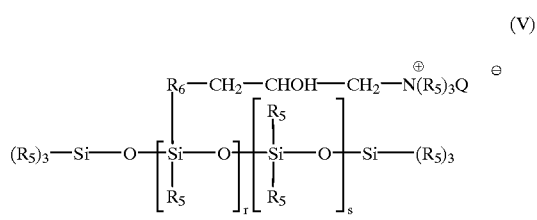

(V)

in which:
R$_5$ represents a monovalent hydrocarbon radical having from 1 to 18 carbon atoms, and in particular a C$_1$–C$_{18}$ alkyl or C$_2$–C$_{18}$ alkenyl radical, for example methyl;
R$_6$ represents a divalent hydrocarbon radical, in particular a C$_1$–C$_{18}$ alkylene radical or a divalent C$_1$–C$_{18}$, for example C$_1$–C$_{18}$, alkylenoxy radical connected to the Si by an SiC bond;
Q$^-$ is an anion such as a halide ion, in particular chloride, or an organic acid salt (acetate, etc.);
r represents an average statistical value from 2 to 20 and in particular from 2 to 8;
s represents an average statistical value from 20 to 200 and in particular from 20 to 50.

Such aminosilicones are described more particularly in U.S. Pat. No. 4,185,087, the disclosure of which is specifically incorporated by reference herein.

A silicone which falls within this class is the silicone sold by the company Union Carbide under the name "UCAR SILICONE ALE 56".

d) quaternary ammonium silicones of formula:

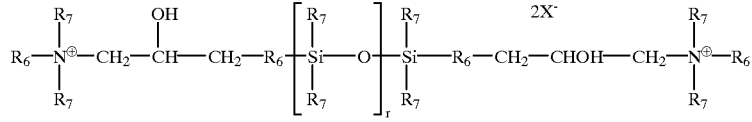

(VI)

in which:
R$_7$ independently represent a monovalent hydrocarbon radical having from 1 to 18 carbon atoms, and in particular a C$_1$–C$_{18}$ alkyl radical, a C$_2$–C$_{18}$ alkenyl radical or a ring comprising 5 or 6 carbon atoms, for example methyl;
R$_6$ independently represent a divalent hydrocarbon radical, in particular a C$_1$–C$_{18}$ alkylene radical or a divalent C$_1$–C$_{18}$, for example C$_1$–C$_8$, alkylenoxy radical connected to the Si by an SiC bond;
R$_8$ independently represent a hydrogen atom, a monovalent hydrocarbon radical having from 1 to 18 carbon atoms, and in particular a C$_1$–C$_{18}$ alkyl radical, a C$_2$–C$_{18}$ alkenyl radical or a radical —R$_6$—NHCOR$_7$;
X$^-$ is an anion such as a halide ion, in particular chloride, or an organic acid salt (acetate, etc.);
r represents an average statistical value from 2 to 200 and in particular from 5 to 100.

These silicones are described, for example, in application EP-A-0 530,974, the disclosure of which is specifically incorporated by reference herein.

Silicones falling within this class are the silicones sold by the company Goldschmidt under the names ABIL QUAT 3270, ABIL QUAT 3272 and ABIL QUAT 3474.

e) aminosilicones of formula (VII):

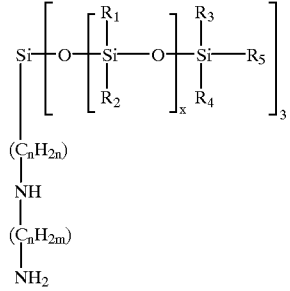

(VII)

in which:
R$_1$, R$_2$, R$_3$ and R$_4$ independently denote a C$_1$–C$_4$ alkyl radical or a phenyl group,
R$_5$ denotes a C$_1$–C$_4$ alkyl radical or a hydroxyl group,
n is an integer ranging from 1 to 5,
m is an integer ranging from 1 to 5,
and in which x is selected such that the amine number ranges from 0.01 to 1 meq/g.

According to the invention, the aminosilicones can be in the form of an oil, of aqueous, alcoholic or aqueous-alcoholic solutions, in the form of a dispersion or an emulsion.

One particularly advantageous embodiment is their use in the form of emulsions, in particular in the form of microemulsions or nanoemulsions.

The product sold under the name "CATIONIC EMULSION DC 929" by the company Dow Corning, which comprises, besides amodimethicone, a cationic surfactant derived from tallow fatty acids, referred to as tallotrimonium (CTFA), in combination with a nonionic surfactant, known under the name "NONOXYNOL 10", can be used for example.

The product sold under the name "CATONIC EMULSION DC 939" by the company Dow Corning, which comprises, besides amodimethicone, a cationic surfactant, trimethylcetylammonium chloride, in combination with a nonionic surfactant, trideceth-12, can also be used for example.

Another commercial product which can be used according to the invention is the product sold under the name "DOW CORNING Q2 7224" by the company Dow Corning, containing, in combination, the trimethylsilylamodimethicone of formula (IV), a nonionic surfactant of formula: $C_8H_{17}$—$C_6H_4$—$(OCH_2CH_2)_n$—OH in which n=40, also known as octoxynol-40, another nonionic surfactant of formula: $C_{12}H_{25}$—$(OCH_2$—$CH_2)_n$—OH in which n=6, also known as isolaureth-6, and glycol.

(i) Cationic polymer(s):

For the purposes of the present invention, the expression "cationic polymer" denotes any polymer containing cationic groups and/or groups that are ionizable into cationic groups.

The compositions in accordance with the invention also necessarily comprise a cationic polymer selected from homopolymers containing, as main constituent of the chain, units corresponding to formula (I) or (I'):

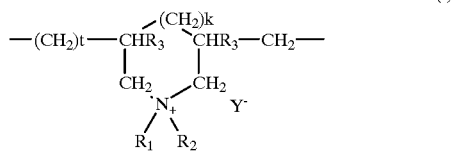

(I)

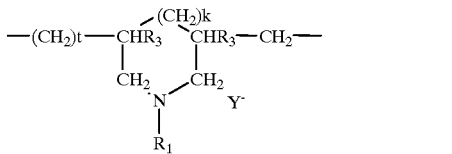

(I')

in which k and t are equal to 0 or 1, the sum k+t being equal to 1;

$R_3$ denotes a hydrogen atom or a methyl radical;

$R_1$ and $R_2$ independently denote an alkyl group having from 1 to 22 carbon atoms, a hydroxyalkyl group in which the alkyl group preferably has 1 to 5 carbon atoms, a lower (1 to 5 carbon atoms) amido alkyl group, or $R_1$ and $R_2$ can denote, together with the nitrogen atom to which they are attached, heterocyclic groups such as piperidyl or morpholinyl; and $Y^-$ is an anion such as bromide, chloride, acetate, borate, citrate, tartrate, bisulphate, bisulphite, sulphate or phosphate.

These polymers are described in particular in French patent 2,080,759, in its Certificate of Addition 2,190,406, the disclosures of which are specifically incorporated by reference herein, or in U.S. Pat. Nos. 3,996,146 and 3,288,770, the disclosures of which are specifically incorporated by reference herein.

Preferably, $R_1$ and $R_2$ independently denote methyl or ethyl and $R_3$ denotes a hydrogen atom.

The cationic polymers used have a weight-average molecular weight preferably ranging from approximately 5000 to approximately $5 \times 10^6$ approximately, and more preferably from approximately $10^4$ to approximately $5 \times 10^5$.

Among the polymers defined above, mention may be made more particularly of dimethyldiallylammonium chloride homopolymers such as the one sold under the name "MERQUAT® 100" by the company Calgon.

The compositions in accordance with the invention contain the aminosilicones defined above in weight contents which can range preferably from 0.05% to 10%, more preferably from 0.1% to 5% and even more preferably from 0.2% to 3%, relative to the total weight of the composition.

According to the invention, the cationic polymer(s) can represent preferably from 0.001% to 10% by weight, more preferably from 0.005% to 5% by weight and even more preferably from 0.01% to 3% by weight, of the total weight of the final composition.

The vehicle, or support, for the detergent compositions according to the invention is preferably water or an aqueous-alcoholic solution of a $C_1$–$C_6$ lower alcohol such as ethanol, isopropanol or butanol, or a mixture of water and an alkylene glycol such as propylene glycol and glycol ethers.

The detergent compositions according to the invention have a final pH generally ranging from 3 to 10. More preferably, this pH ranges from 5.5 to 8. The pH can be adjusted to the desired value conventionally by adding a base (organic or inorganic) into the composition, for example aqueous ammonia or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

The compositions in accordance with the invention can contain, in addition to the combination defined above, viscosity modifiers such as electrolytes, or thickeners. Mention may be made in particular of sodium chloride, sodium xylenesulphonate, scleroglucans, xanthan gums, fatty acid alkanolamides, alkanolamides of carboxylic acid alkyl ether optionally oxyethylenated with up to 5 mol of ethylene oxide, such as the product sold under the name "AMINOL A15" by the company Chem Y, crosslinked polyacrylic acids and crosslinked acrylic acid/$C_{10}$–$C_{30}$ alkyl acrylate copolymers. These viscosity modifiers are used in the compositions according to the invention in proportions which may range up to 10% by weight relative to the total weight of the composition.

The compositions in accordance with the invention can also contain up to 5% of pearlescent agents or opacifiers that are well known in the state of the art, such as, for example, sodium or magnesium palmitate, sodium or magnesium stearate or hydroxystearate, acyl derivatives containing a fatty chain, such as monostearates or distearates of ethylene glycol or of polyethylene glycol, fatty-chain ethers such as distearyl ether or 1-hexadecyloxyoctadodecanol.

The compositions in accordance with the invention can optionally also contain other adjuvants whose effect is to improve the cosmetic properties of the hair or the skin. Mention may be made, in this respect, of cationic surfactants, anionic, nonionic, cationic or amphoteric polymers, proteins, proteinhydrolysates, ceramides, pseudoceramides, hydroxy acids, vitamins, panthenol, plant, animal, mineral or synthetic oils, and water-soluble or liposoluble sunscreens.

These compositions can also contain various adjuvants commonly used in cosmetics, such as fragrances, preserving agents, sequestering agents, foam stabilizers and acidifying or basifying agents that are well known in cosmetics.

Needless to say, a person skilled in the art will take care to select this or these optional complementary compounds and/or the amounts thereof such that the advantageous properties intrinsically associated with the combination (washing base+specific cationic polymer +aminosilicone) in accordance with the invention are not, or are not substantially, adversely affected by the addition(s) envisaged.

These compositions can be in the form of relatively thickened liquids, creams or gels and they are mainly suitable for washing and caring for keratin substances such as the skin or the hair.

The compositions according to the invention are preferably used as shampoos for washing and conditioning the hair, and they are applied, in this respect, to wet hair in amounts that are effective to wash them, this application being followed by rinsing with water.

The compositions in accordance with the invention can also be used as shower gels for washing and conditioning the hair and the skin, in which case they are applied to wet hair or skin and are rinsed after application.

The compositions in accordance with the invention can also be used as agents for removing make-up from keratin substances such as the skin, the eyelashes or the eyebrows.

The subject of the invention is also a process for washing and conditioning keratin substances such as the hair, which involves applying an effective amount of a composition as defined above to the said wet substances, followed by rinsing with water after optionally leaving the composition on the keratin substances for a while.

Concrete, but in no way limiting, examples illustrating the invention will now be given.

EXAMPLE 1

Two shampoo compositions, one in accordance with the invention (composition A) and the other a comparative composition (composition B), were prepared:

| | A<br>Invention | B<br>Comparative |
|---|---|---|
| Sodium lauryl ether sulphate (70/30 $C_{12}/C_{14}$) containing 2.2 mol of ethylene oxide, as an aqueous solution containing 70% A.M. (A.M. = active material) | 15.5 g A.M. | 15.5 g A.M. |
| Cocobetaine containing 32% A.M. (*) | 3.2 g A.M. | — |
| Cocoamphodiacetate (Miranol C2M Conc. from RP) | — | 3.2 g A.M. |
| Cationic polymer (**) | 0.6 g | 0.6 g |
| Aminosilicone (***) | 2.45 g A.M. | 2.45 |
| Sodium cetostearyl sulphate | 0.75 g | 0.75 g |
| Mixture of 1-hexadecyloxy-octadodecanol and cetyl alcohol | 2.5 g | 2.5 g |
| Oxyethylenated decyl alcohol ($C_{10}/C_{12}/C_{14}$) | 0.5 g | 0.5 g |
| Citric acid qs pH | 5 | 5 |
| Fragrance, preserving agents | qs | qs |
| Demineralized water qs | 100 g | 100 g |

(*) Dehyton ® AB 30 from Henkel
(**): Dimethyldiallylammonium chloride homopolymer sold under the name Merquat ® 100 (MW 400,000) by the company Calgon
(***): Amodimethicone sold as a cationic emulsion containing 35% active material, under name FLUID DC 939 by the company Dow Corning Shampooing was carried out by applying about 12 g of composition A to premoistened hair. The shampoo was worked into a lather and was then rinsed thoroughly with water.

The same procedure as above was carried out with the comparative composition B.

A panel of experts evaluated the disentangling of the wet hair, the disentangling of the dried damp hair and the softness and smoothness of the dried hair.

All the experts indicated a marked improvement in these properties for hair treated with composition A according to the invention.

EXAMPLE 2

A shampoo of the following composition was prepared:
Sodium lauryl ether sulphate (70/30 by weight $C_{12}/C_{14}$) containing 2.2 mol of ethylene oxide, as an aqueous solution containing 28% A.M. 14 g A.M.
Cocobetaine containing 32% A.M. (*) 3.2 g A.M.
Cationic polymer (**) 0.1 g
Aminosilicone (***) 1.05 g A.M.
Mixture of 1-hexadecyloxyoctadodecanol and cetyl alcohol 2.5 g
Coconut acid monoisopropanolamide 0.6 g
2-Amino-2-methyl-1-propanol 0.125 g
Citric acid qs pH 5.2
Demineralized water qs 100 g (*) Dehyton® AB 30 from Henkel
(**): Dimethyidiallylammonium chloride homopolymer sold under the name MERQUAT® 100 (MW 400,000) by the company Calgon
(***): Amodimethicone sold as a cationic emulsion containing 35% active material, under the name FLUID DC 939 by the company Dow Corning

We claim:

1. A detergent composition comprising, in a cosmetically acceptable medium, (A) a washing base comprising at least one alkyl ether sulphate anionic surfactant and at least one $C_8$–$C_{20}$ alkylbetaine amphoteric surfactant, and (B) a conditioning system comprising at least one aminosilicone and at least one cationic polymer selected from homopolymers containing, as the main constituent of the chain, repeating units selected from formulae (I) and (I'):

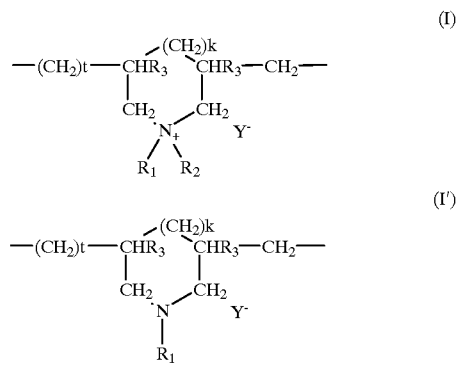

in which
k and t are equal to 0 or 1 and the sum k+t equals 1;
$R_3$ independently denote a hydrogen atom or a methyl radical;
$R_1$ and $R_2$ independently denote an alkyl group having from 1 to 22 carbon atoms, a hydroxyalkyl group in which the alkyl group has from 1 to 5 carbon atoms, a lower (1 to 5 carbon atoms) amido alkyl group, or $R_1$ and $R_2$ can denote, together with the nitrogen atom to which they are attached, a heterocyclic group; and
$Y^-$ is an anion.

2. A detergent composition according to claim 1, wherein said heterocyclic group is selected from piperidyl and morpholinyl and wherein said anion is selected from bromide, chloride, acetate, borate, citrate, tartrate, bisulphate, bisulphite, sulphate and phosphate.

3. A detergent composition according to claim 1, wherein said at least one cationic polymer is selected from dimethyidiallylammonium chloride homopolymers.

4. A detergent composition according to claim 1, wherein said at least one alkyl ether sulphate anionic surfactant is selected from salts of alkyl ether sulphates; alkylamido ether sulphates; alkylaryl ether sulphates; and alkyl ether sulphosuccinates.

5. A detergent composition according to claim 4, wherein said alkyl radicals contain from 8 to 24 carbon atoms and said aryl radicals denote a phenyl or benzyl group.

6. A detergent composition according to claim 1, wherein said at least one alkyl ether sulphate anionic surfactant is selected from $C_8$–$C_{14}$ alkyl ether sulphate salts.

7. A detergent composition according to claim 6, wherein said at least one alkyl ether sulphate anionic surfactant is selected from $C_{12}$–$C_{14}$ alkyl ether sulphate salts.

8. A detergent composition according to claim 1, wherein said at least one $C_8$–$C_{20}$ alkylbetaine amphoteric surfactant is a $C_{10}$–$C_{14}$ alkylbetaine amphoteric surfactant.

9. A detergent composition according to claim 8, wherein said at least one $C_8$–$C_{20}$ alkylbetaine amphoteric surfactant is a $C_{12}$–$C_{14}$ alkylbetaine amphoteric surfactant.

10. A detergent composition according to claim 1, wherein said at least one aminosilicone is selected from:
(a) polysiloxanes referred to in the CTFA dictionary as "amodimethicone" and corresponding to the formula:

$$\text{HO}-\left[\begin{array}{c}\text{CH}_3\\|\\\text{Si}-\text{O}\\|\\\text{CH}_3\end{array}\right]_{x'}\left[\begin{array}{c}\text{OH}\\|\\\text{Si}-\text{O}\\|\\(\text{CH}_2)_3\\|\\\text{NH}\\|\\(\text{CH}_2)_2\\|\\\text{NH}_2\end{array}\right]_{y'}\text{H} \quad (II)$$

in which
x' and y' independently are integers resulting in a weight-average molecular weight ranging from 5000 to 500,000;

(b) aminosilicones corresponding to the formula:

$$R'_a G_{3-a}-\text{Si}(\text{OSiG}_2)_n-(\text{OSiG}_b R'_{2-b})_m-\text{O}-\text{SiG}_{3-a}-R'_a \quad (III)$$

in which:
G is independently a hydrogen atom or a phenyl, OH or $C_1$–$C_8$ alkyl group, a independently denotes the number 0 or an integer from 1 to 3, b independently denotes 0 or 1, m and n are numbers such that the sum (n+m) ranges from 1 to 2000, wherein n denotes a number ranging from 0 to 1999 and m denotes a number ranging from 1 to 2000;

R' independently is a monovalent radical of formula $-C_q H_{2q} L$, wherein q is a number from 2 to 8 and L is an optionally quaternized amine group selected from:

—NR"—CH$_2$—CH$_2$—N'(R")$_2$

—N(R")$_2$

—N$\oplus$(R")$_3$A$^-$

—NH$\oplus$(R")$_2$A$^-$

—NH$_2\oplus$(R")A$^-$

—N(R")—CH$_2$—CH$_2$—N$\oplus$R"H$_2$A$^-$, in which R" independently denotes hydrogen, phenyl, benzyl, or a saturated monovalent hydrocarbon radical, and A$^-$ represents a halide ion.

(c) aminosilicones corresponding to the formula:

$$(R_5)_3-\text{Si}-\text{O}-\left[\begin{array}{c}R_5\\|\\\text{Si}-\text{O}\\|\\R_5\end{array}\right]_r\left[\begin{array}{c}R_6-\text{CH}_2-\text{CHOH}-\text{CH}_2-\text{N}^\oplus(R_5)_3 Q^\ominus\\|\\\text{Si}-\text{O}\\|\\R_5\end{array}\right]_s\text{Si}-(R_5)_3 \quad (V)$$

in which:
$R_5$ independently represents a monovalent hydrocarbon radical having from 1 to 18 carbon atoms, $R_6$ independently represents a divalent hydrocarbon radical, $Q^-$ is an anion;

r represents an average statistical value from 2 to 20;

s represents an average statistical value from 20 to 200;

d) quaternary ammonium silicones of formula:

$$R_8-\overset{R_7}{\underset{R_7}{\text{N}^+}}-\text{CH}_2-\overset{\text{OH}}{\underset{}{\text{CH}}}-\text{CH}_2-R_6-\left[\begin{array}{c}R_7\\|\\\text{Si}-\text{O}\\|\\R_7\end{array}\right]_r\overset{R_7}{\underset{R_7}{\text{Si}}}-R_6-\text{CH}_2-\text{CHOH}-\text{CH}_2-\overset{R_7}{\underset{R_7}{\text{N}^+}}-R_8 \quad 2X^- \quad (VI)$$

in which:
$R_7$ independently represents a monovalent hydrocarbon radical having from 1 to 18 carbon atoms;

$R_6$ independently represents a divalent hydrocarbon radical;

$R_8$ independently represents a hydrogen atom or a monovalent hydrocarbon radical having from 1 to 18 carbon atoms;

$X^-$ is an anion;

r represents an average statistical value from 2 to 200;

e) aminosilicones of formula (Vll):

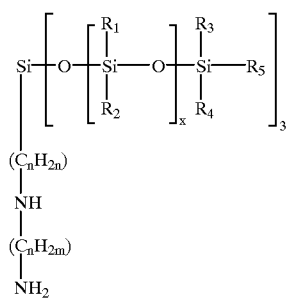

in which:
R$_1$, R$_2$, R$_3$ and R$_4$ independently denote a C$_1$–C$_4$ alkyl radical or a phenyl group,
R$_5$ denotes a C$_1$–C$_4$ alkyl radical or a hydroxyl group,
n is an integer ranging from 1 to 5,
m is an integer ranging from 1 to 5,
wherein x is selected to provide an amine number ranging from 0.01 to 1 meq/g.

11. A detergent composition according to claim 10, wherein at least one of the following is true:
in formula (III),
  G is methyl;
  a is 0;
  b is 1;
  the sum n+m ranges from 50 to 150;
  n ranges from 49 to 149;
  m ranges from 1 to 10;
  R" is an alkyl radical having from 1 to 20 carbon atoms;
  A$^-$ represents fluoride, chloride, bromide or iodide;
in formula (V),
R$_5$ represents a C$_1$–C$_{18}$ alkyl or C$_2$–C$_{18}$ alkenyl radical;
  R$_6$ represents a C$_1$–C$_{18}$ alkylene radical or a divalent C$_1$–C$_{18}$ alkylenoxy radical connected to the Si by an SiC bond;
  Q$^-$ is a halide ion or an organic acid salt;
  r represents an average statistical value from 2 to 8;
  s represents an average statistical value from 20 to 50;
in formula (VI),
  R$_7$ represents a C$_1$–C$_{18}$alkyl radical, a C$_2$–C$_{18}$ alkenyl radical or a ring comprising 5 or 6 carbon atoms;
  R$_8$ represents a C$_1$–C$_{18}$ alkyl radical, a C$_2$–C$_{18}$ alkenyl radical or a radical —R$_6$—NHCOR$_7$;
  X$^-$ is a halide ion or an organic acid salt; and
  r represents an average statistical value from 5 to 100.

12. A detergent composition according to claim 11, wherein at least one of the following is true:
in formula (V),
  R$_5$ is methyl;
  R$_6$ is a divalent C$_1$–C$_8$ alkylenoxy radical connected to the Si by an SiC bond;
  Q$^-$ is chloride or acetate;
in formula (VI),
  R$_7$ is methyl; and
  X$^-$ is chloride or acetate.

13. A detergent composition according to claim 1, wherein said at least one alkyl ether sulphate anionic surfactant is present in an amount ranging from 1 to 50% by weight relative to the total weight of said composition.

14. A detergent composition according to claim 13, wherein said at least one alkyl ether sulphate anionic surfactant is present in an amount ranging from 5 to 20% by weight relative to the total weight of said composition.

15. A detergent composition according to claim 1, wherein said at least one C$_8$–C$_{20}$ alkylbetaine amphoteric surfactant is present in an amount ranging from 1 to 50% by weight relative to the total weight of said composition.

16. A detergent composition according to claim 15, wherein said at least one C$_8$–C$_{20}$ alkylbetaine amphoteric surfactant is present in an amount ranging from 1 to 20% by weight relative to the total weight of said composition.

17. A detergent composition according to claim 1, wherein said at least one cationic polymer is present in an amount ranging from 0.001% to 10% relative to the total weight of said composition.

18. A detergent composition according to claim 17, wherein said at least one cationic polymer is present in an amount ranging from 0.005% to 5% relative to the total weight of said composition.

19. A detergent composition according to claim 18, wherein said at least one cationic polymer is present in an amount ranging from 0.01% to 3% relative to the total weight of said composition.

20. A detergent composition according to claim 1, wherein said at least one aminosilicone is present in an amount ranging from 0.05% to 10% relative to the total weight of said composition.

21. A detergent composition according to claim 20, wherein said at least one aminosilicone is present in an amount ranging from 0.1% to 5% relative to the total weight of said composition.

22. A detergent composition according to claim 21, wherein said at least one aminosilicone is present in an amount ranging from 0.2% to 3% relative to the total weight of said composition.

23. A detergent composition according to claim 1 for cleaning and/or conditioning and/or removing make-up from keratin substances.

24. A detergent composition according to claim 1, wherein said washing base is present in an amount ranging from 2 to 50% by weight relative to the total weight of said composition.

25. A detergent composition according to claim 24, wherein said washing base is present in an amount ranging from 10 to 35% by weight relative to the total weight of said composition.

26. A detergent composition according to claim 25, wherein said washing base is present in an amount ranging from 12 to 25% by weight relative to the total weight of said composition.

27. A detergent composition according to claim 1, wherein said at least one aminosilicone is in the form of an oil, an aqueous, alcoholic or aqueous-alcoholic solution, a dispersion or an emulsion.

28. A detergent composition according to claim 27, wherein said emulsion is a microemulsion or a nanoemulsion.

29. A detergent composition according to claim 1, wherein said cosmetically acceptable vehicle comprises water or an aqueous-alcoholic solution of a C$_1$–C$_6$ lower alcohol, or water and an alkylene glycol.

30. A detergent composition according to claim 29, wherein said C$_1$–C$_6$ lower alcohol is ethanol, isopropanol or butanol.

31. A detergent composition according to claim 29, wherein said alkylene glycol is selected from propylene glycol and glycol ethers.

32. A detergent composition according to claim 1, wherein said composition has a pH ranging from 3 to 10.

33. A detergent composition according to claim 32, wherein said composition has a pH ranging from 5.5 to 8.

34. A detergent composition according to claim 1, wherein said composition further comprises at least one additive selected from viscosity modifiers, pearlescent agents or opacifiers, adjuvants to improve the cosmetic properties of hair or skin, fragrances, preserving agents, sequestering agents, foam stabilizers, acidifying agents, and basifying agents.

35. A detergent composition according to claim 1, wherein said composition is in the form of a thickened liquid, a cream, or a gel.

36. A process for washing a keratin substance comprising wetting said keratin substance, applying an effective amount to said keratin substance of at least one composition comprising, in a cosmetically acceptable medium,
(A) a washing base comprising at least one alkyl ether sulphate anionic surfactant and at least one $C_8$–$C_{20}$ alkylbetaine amphoteric surfactant, and
(B) a conditioning system comprising at least one aminosilicone and at least one cationic polymer selected from homopolymers containing, as the main constituent of the chain, repeating units selected from formulae (I) and (I'):

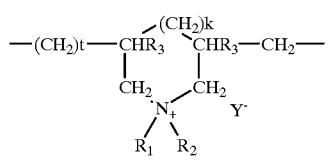

(I)

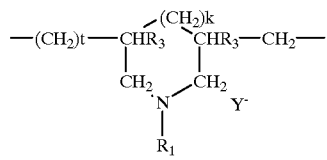

(I')

in which k and t are equal to 0 or 1 and the sum k + t equals 1;

$R_3$ independently denote a hydrogen atom or a methyl radical;

$R_1$ and $R_2$ independently denote an alkyl group having from 1 to 22 carbon atoms, a hydroxyalkyl group in which the alkyl group has from 1 to 5 carbon atoms, a lower (1 to 5 carbon atoms) amido alkyl group, or $R_1$ and $R_2$ can denote, together with the nitrogen atom to which they are attached, a heterocyclic group; and $Y^-$ is an anion, optionally leaving the composition on the keratin substance for a period of time, and rinsing said keratin substance with water.

37. A process according to claim 36, wherein said keratin substance is human hair.

38. A process according to claim 36, wherein said keratin substance is human skin.

39. A detergent composition according to claim 1, wherein $R_1$ and $R_2$ independently denote methyl or ethyl and $R_3$ denotes a hydrogen atom.

* * * * *

UNITED STATES PATENT AND TRADEMARK OFFICE
CERTIFICATE OF CORRECTION

PATENT NO.: 6,159,914

DATED: December 12, 2000

INVENTOR(S): Sandrine DECOSTER et al.

It is certified that an error appears in the above-identified patent and that said Letters Patent is hereby corrected as shown below:

Claim 3, col. 11, lines 7-8, "dimethyidiallylammonium" should read --dimethyldiallylammonium--.

Title page, item [54], lines 2-4 of Title, delete "COMPRISING AN AMINOSILICONE AND A CATIONIC POLYMER".

Signed and Sealed this

Eighth Day of May, 2001

*Attest:*

NICHOLAS P. GODICI

*Attesting Officer*         *Acting Director of the United States Patent and Trademark Office*